United States Patent [19]
Horvath

[11] Patent Number: 5,165,932
[45] Date of Patent: Nov. 24, 1992

[54] THERAPEUTICAL COMPOSITIONS AGAINST PSORIASIS

[75] Inventor: Ferenc Horvath, Szalai Attila, Hungary

[73] Assignee: Unipharma Co., Ltd., Budapest, Hungary

[21] Appl. No.: 397,429

[22] PCT Filed: Dec. 23, 1987

[86] PCT No.: PCT/HU87/00060
§ 371 Date: Sep. 15, 1989
§ 102(e) Date: Sep. 15, 1989

[87] PCT Pub. No.: WO89/05651
PCT Pub. Date: Jun. 29, 1989

[51] Int. Cl.$^5$ .............................................. A61K 35/78
[52] U.S. Cl. ............................... 424/195.1; 514/863; 514/886; 514/887
[58] Field of Search ................... 424/195.1; 514/886, 514/887, 863

[56] References Cited

U.S. PATENT DOCUMENTS 4,569,839 2/1986 Grollier et al. .................. 424/195.1
4,758,433 7/1988 Johnson et al. .................. 424/195.1

OTHER PUBLICATIONS

"The Herb Book"; John B. Lust, First Ed. Bendedict Lust Publications.

Primary Examiner—John W. Rollins
Attorney, Agent, or Firm—Ladas & Parry

[57] ABSTRACT

The invention relates to therapeutical compositions on medical herb basis for the treatment of psoriasis and the preparation of the same. A further object of the invention in the use of medical herbs as listed below in the treatment of psoriasis, rheumatism and asthmatic dyspnoea. The medical herbs used in the invention are as follows:
Allium sativum /garlic/,
Urtica dioica /common nettle/,
Chelidonium majus /milkweed/,
Veronica officinalis /veronica/,
Calendula officinalis /calendula or marigold/,
Achillea herba /millefolium/ /yarrow/,
Fumaria officinalis /fumitory, earth-gall/.

1 Claim, No Drawings

5,165,932

THERAPEUTICAL COMPOSITIONS AGAINST PSORIASIS

TECHNICAL FIELD

The present invention relates to therapeutical compositions on medicinal herb basis for the treatment of psoriasis. An other object of the invention is the preparation of the said compositions. A further object of the invention is the use of the medicinal herbs as listed below in the treatment of psoriasis, rheumatism and asthmatic dyspnoea.

BACKGROUND ART

Psoriasis constitutes one of the most common chronic skin diseases. Even nowdays the origin thereof has not been clarified, presumably it is based ona complex effect of various factors within the human organism. In pathological point of view it is a chronic dermatitis, with unnaturally high epithelial cell proliferation on the surface, and hyperaemia and dense lymphocita-infiltration on the corium side. Essentially, the disease may start in any period of life and exists for decades with periodic eruptions and/or permanent centres. Psoriasis most frequently occurs on the tensive surfaces of limbs, on hairy scalp and traumatic skin parts, respectively.

A large number of methods have already been used for the treatment of psoriasis. B. Issekutz and L. Issekutz, Gyógyszerrendelés, Medicina, Budapest, 1979 gives a comprehensive review on the methods and materials used for the treatment of psoriasis. These treatments are, however, almost exclusively of symptomatic character only as no composition against psoriasis has been provided which would result in a total curative effect or at least in a suppression of the disease for a longer period, i.e. for some years. The literature suggest for the treatment of psoriasis e.g. vitamins $B_{12}$ or A, different creams containing arsenic acid or arsenates, cooling ointments containing aluminum acetate, desquamatories with resorcine as active ingredient, lotions containing tallium acetate, as well as other compositions which contain salycilic acid or the derivatives thereof. The ointment Psoriasin contains 2,2'-dichlorodiethyl-sulfide/mustardgas/, the said ointment may be used, however, only once daily as a thin smear. The tar ointments have the disadvantage that only a part of the skin area may be treated once and even with a short contact period. The salycilic acid compositions serve for a desquamation of the skin surface and as such they are again of symptomatic effect only as the disease will not be terminated.

In the popular therapy a wide scale of medicinal herbs is used against skin diseases. No medicinal herb has been known, however, for the effective treatment of psoriasis.

Accordingly, the present invention aims to provide a composition which not only serves for symptomatic treatment of psoriasis, but also suppresses the same finally or at least for a long period.

The invention is based on the recognition that some combinations of medicinal herbs when used externally on the skin, provide a method of treatment and therapeutical composition, respectively, which fulfil the requirements as aimed above.

DISCLOSURE OF INVENTION

The present invention provides therapeutical compositions against psoriasis which comprises a combination of different medicinal herbs. Another object of the invention is the process for preparing the above therapeutical compositions. Another object of the present invention is the use of certain combinations of medical herbs in the treatment of psoriasis, rheumatic symptoms and asthmatic dyspnoea.

According to the present invention the therapeutical compositions comprise the extracts of the following drug plants:
Allium sativum/garlic/,
Urtica dioica/common nettle/,
Chelidonium majus/milkweed/,
Veronica officinalis/veronica/,
Calendula officinalis/calendula or marigold/,
Achillea herba/millefolium/ /yarrow/,
Fumaria officinalis/fumitory, earth-gall/.

The therapeutical compositions according to the present invention comprise suitably the extracts of at least three of the above medical herbs.

In the natural therapy the garlic is especially used against senescense symptoms, arteriosclerosis, hypertonia, diarrhoea, intestinal worms, etc. The juice thereof is said to be effective against warts as well. The plant comprises garlic oil, alliin and allicin as pharmacologically active ingredients. The latter may be regarded as antibiotic but possesses insecticidal effect as well.

The main amount of the common nettle drug is used in the preparation of chlorophyll. The tea thereof is used against rheumatism, gout, diabetes, oedema, urticaria, catarrhal cystitis, hypertonia, gastroenteritis, exanthems, renal gravel, etc. Externally it has the use against haemorrhoid as sitting bath, against exanthems as lotion, against psilosis, seborrhea and oily hair as hair wash.

The milkweed belongs to the family of Papaveraceae. The drug thereof is used in the preparation of medicines against bilious and liver disorders, as well as gastroenteritis also in industrial scale. The fresh juice of the plant serves for treating warts and corns.

The tea of veronica is known as antitussive and against asthma and cardiac asthma.

The decoction of calendula may be used internally against gastric and intestinal ulcer and externally for packing of slowly healing wounds and ulcers. It is also known as colouring agent in foodstuffs, medicines and drinks.

The drugs of yarrow are appetizers and digestives. They can be used as anticonvulsiva for promoting the bile and liver function, in the treatment of ureteral and respiratory disorders and as hypotensive agents, respectively. Externally, the concoction thereof is useful wash and lotion against gingival, ocular and general inflammations.

The tea of fumitory has appetizing, digestive, laxative and choleretic effect. It is used against icterus as well.

During our experiments it has been established that the above drugs, when used separately, did not provide sufficient curative effect against psoriasis. Surprisingly, it has been found that certain combinations of the same which comprise preferably at least two or more of the above medical herbs a high curative effect might be obtained. Therefore the compositions according to the present invention comprise suitably at least three of the extracts of the above drug plants. Of course, the therapeutical compositions may also contain more than three active ingredients, e.g. all the seven as well.

In the compositions according to the present invention the extracts of the above medicinal herbs are preferably those prepared with an oil. As oil, vegetable, animal and mineral oils can be used. During the extraction preferably paraffin oil or sunflower oil is used. The compositions according to the present invention are prepared preferably in a form suitable for the treatment of skin. For these purposes the oily extract of the medicinal herbs itself or the mixture thereof with at least one additive generally used in the preparation of external topical compositions may be used. Especially preferred additive is the paraffin oil which may be of medical grade/PH. HG. VII/or cosmetic grade as well. The compositions according to the present invention may also contain further additives known per se, e.g. colouring agents, flavouring agents, etc. As flavouring and colouring agents not only the additives generally used by the pharmaceutical industry, but also additional medical herb extracts can be used. Such medical herbs are e.g. the followings:

Calami rhizoma/sweet-sedge/,
Quercus cortex/oak-bark/,
Salix alba/cortex/ /willow cortex/,
Taraxi radix/daudelion/ /cortex/,
Alcanae radix/alkanna/.

The preparation of the therapeutical compositions is accomplished preferably by pouring the suitable extraction oil on the appropriately crushed, preferably ground dry medical herb, and keeping the mixture on elevated temperature for a longer period. Afterwards the supernatant is separated from the solid plant residue and the supernatant is used for the treatment as such or for mixing with additional additives to prepare therapeutical compositions. In case when besides the active ingredients medical herbs are also used as additives, it is preferred to introduce the latter in the extraction step.

The period and temperature of the extraction procedure is not critical, any temperature which does not result in thermal degradation of the active substances in the drugs may be used while the extraction period should be long enough to provide a reasonable extraction grade at the temperature used. Preferably the extraction is carried out for 12 to 48 hours, at a temperature of 40° to 70° C.

According to the preferred embodiment of the process the extraction is carried out for 24 hours at 60° C. According to the most preferred embodiment of the present invention during the extraction carried out with the oil not the whole garlic but the solid material content having previously been extracted with an alcohol is used. By this previous extraction the appearance of the composition can substantially be improved. The alcoholic extraction of garlic can be carried out with any liquid alcohol, preferably methanol and ethanol. The use of 96% ethanol is most preferred. The temperature and period of the alcoholic extraction is not critical, it can be carried out preferably below or on the boiling point of the alcohol used therein. The extraction is preferably carried out also at 60° C. for 24 hours under continuous stirring.

After the extraction the alcohol is removed from the solid material, preferably by filtering, the solids are dried, preferably in vacuo at 50° to 60° C. and then added to the dry material of the oil extraction.

During our experiments a large number of patients were treated with the compositions according to the present invention and in 90% of the treatments after several weeks' use the symptoms of psoriasis completely disappeared and did not re-appear. Of course, the treatment period strongly depends on the grade of disease and age and physical condition of the patient.

During our experiments it has also been surprisingly found that the medical herbs used in the above compositions and/or the compositions themselves are not only active against psoriasis but also against rheumatism and asthmatic dyspnoea. Accordingly, another object of the present invention is the use of the above medical herbs, the mixtures thereof and the compositions containing the same in the treatment of rheumatism and asthmatic dyspnoea.

BEST MODE OF CARRYING OUT THE INVENTION

The present invention is further illustrated in the following example without limiting the scope of protection to the embodiment illustrated therein.

EXAMPLE 10 kg of garlic was crushed and ground and put into an appropriate container. 7,5 liter of 96% ethanol was poured on and the mixture was kept for 24 hours at 60° C. while continuously stirring. The supernatant was separated and the residue was dried in vacuo at 50° to 60° C. until disappearing of the alcohol smell. The dry garlic material, pre-treated as above, was added to the following crushed and ground medical herb dry material:

| | |
|---|---|
| Urtica dioica /common nettle/ | 300 g, |
| Chelidonium majus /milkweed/ | 300 g, |
| Veronica officinalis /veronica/ | 300 g, |
| Calendula officinalis /calendula/ | 300 g, |
| Achillea herba /yarrow/ | 200 g, |
| Fumaria officinalis /fumitory/ | 200 g, |
| Calami rhizoma /sweet-sedge/ | 200 g, |
| Quercus cortex /oak-bark/ | 100 g, |
| Salix alba /cortex/ /willow cortex/ | 300 g, |
| Taraxi radix /daudelion/ /cortex/ | 300 g, |
| Alcanae radix /alkanna/ | 5 g. |

The crushed dry material was mixed 90 liter of paraffin oil was poured thereon and the mixture thus obtained was stirred for 24 hours at 60° C. The dry material was separated by centrifuging and if the extract was turbid, filtered. To the clear oil composition thus obtained 10 liter of sunflower oil was added and filled into appropriate bottles or other containers. Thus, compositions against psoriasis, ready for use were obtained.

In the compositions according to the invention any of the seven major components may be present in 0 to 60% of the total dry weight of active ingredients. The garlic may be present even in a higher concentration, i.e. up to 90%.

I claim:

1. An oil-based plant extract useful in the topical treatment of psoriasis which comprises an extract obtained by heating crushed plant material with topically acceptable vegetable or mineral oil at a temperature of from 40°–70° C. and separating and recovering the oily phase obtained wherein said plant material consists essentially of dry residue after alcohol extraction of garlic and the following medical herbs urtica dioica, veronica officinalis, Calendula officinalis, Achillea herba, Fumaria officinalis, Calami rhizoma, Quercus cortex, Salix alba cortex, Taraxi radix cortex and Alcanae radix in a ratio of about 60:60:60:60:40:40:40:20:60:60:1.

* * * * *